United States Patent
Sim et al.

(10) Patent No.: US 6,276,192 B1
(45) Date of Patent: Aug. 21, 2001

(54) GAS DETECTING SENSOR AND DEVICE FOR CONTROLLING VENTILATION SYSTEMS

(75) Inventors: Hae Kyung Sim; Cheol Lim, both of Seoul (KR)

(73) Assignee: Auto Electronic Corporation, Seoul (KR)

( * ) Notice: Subject to any disclaimer, the term of this patent is extended or adjusted under 35 U.S.C. 154(b) by 0 days.

(21) Appl. No.: 09/351,176

(22) Filed: Jul. 12, 1999

(30) Foreign Application Priority Data

Apr. 14, 1999 (KR) .................................................. 99-13114

(51) Int. Cl.[7] .............................. G01N 27/12; B60H 3/00
(52) U.S. Cl. ..................... 73/25.01; 73/23.31; 73/25.05; 73/31.01; 73/31.02; 73/31.05; 73/31.06; 422/94; 454/75
(58) Field of Search ............................... 73/23.31, 25.01, 73/25.05, 31.01, 31.02, 31.03, 31.05, 31.06; 422/94, 98; 454/75

(56) References Cited

U.S. PATENT DOCUMENTS

| | | | |
|---|---|---|---|
| 5,217,692 | * | 6/1993 | Rump et al. ..................... 73/31.05 X |
| 5,320,577 | * | 6/1994 | Tooru et al. ............................ 454/75 |
| 5,725,425 | * | 3/1998 | Rump et al. ..................... 73/23.31 X |
| 6,004,201 | * | 12/1999 | Rump ............................... 73/23.31 X |

* cited by examiner

Primary Examiner—Daniel S. Larkin
(74) Attorney, Agent, or Firm—Dykema Gossett PLLC

(57) ABSTRACT

There are provided with a gas detecting sensor and a gas detecting device for controlling a ventilation system of a vehicle using the gas detecting sensor. The gas detecting sensor of the present invention includes two kinds of gas sensing layers separately formed and a heater assembly for heating the two sensing layers to different temperatures. The gas detecting device includes: a sensor signal detecting unit for detecting a gas based upon a parallel resistance value obtained by connecting the two kinds of sensing layers of the gas detecting sensor to each other in parallel; a heater drive unit for periodically adjusting the heater to a gasoline exhaust gas sensing temperature and to a diesel exhaust gas sensing temperature; a pulse width modulation (PWM) signal converting unit for generating a differential waveform signal corresponding to the variation of a parallel resistance from the sensor signal detecting unit and converting the differential waveform signal into a PWM signal; and a control unit for controlling the heater drive unit and the PWM signal converting unit, receiving and estimating a sensor signal in the form of a digital signal of the PWM signal, determining a pollution level based upon the estimation, and controlling a ventilation system.

7 Claims, 8 Drawing Sheets

GAS DETECTING SENSOR AND DEVICE FOR CONTROLLING VENTILATION SYSTEMS

BACKGROUND OF THE INVENTION

1. Field of the Invention

The present invention relates to an improved digital gas detecting device for detecting a pollution level of the air in the vicinity of a vehicle and controlling a ventilation system of the vehicle, and more particularly, to a gas detecting sensor having a novel structure for detecting concentrations of a gasoline gas and a diesel gas and a gas detecting device for estimating a pollution level of the air around a vehicle using the gas detecting sensor and controlling a ventilation system.

2. Description of Related Art

A typical gas detecting sensor is a semiconductor sensor using tin dioxide as an active layer. This typical gas detecting sensor has a defect that it cannot sense two kinds of exhaust gases generated by a gasoline vehicle and a diesel vehicle all together. To sense both exhaust gases together, two sensors should be used. A tin dioxide ($SnO_2$) sensor is used to detect the gasoline exhaust gas and a tungsten trioxide ($WO_3$) sensor is used to detect the diesel exhaust gas. However, if two sensors are used, a sensor installation structure and a sensing circuit should be constituted in dual, thereby increasing the size and cost of the gas detecting device.

There have been provided with gas detecting sensors doped with sensing material comprising a compound of various metallic oxides, for detecting gases based upon increase/decrease of resistance caused by the effects of typical gases. However, when only one sensor is used, it is difficult to separate a sensor signal generated due to gasoline exhaust gas from a sensor signal generated due to diesel gas exhaust gas. Besides, complicated sensor signal conversion and signal processing is required. Moreover, when using the sensor having a metallic oxide compound, it may happen that the sensor wrongly senses polluted air and performs a wrong operation with respect to the ventilation system if very harmful material has influenced the sensor device at constant concentration for a long time, for example, if the vehicle has been parked in a very polluted underground parking lot for a long time.

SUMMARY OF THE INVENTION

Accordingly, the present invention is directed to a gas detecting sensor and a gas detecting device for controlling ventilation systems that substantially obviates one or more of the limitations and disadvantages of the related art.

An objective of the present invention is to provide a gas detecting sensor having a novel structure and a gas detecting device for simply separating a gasoline exhaust gas sensing signal from a diesel exhaust gas sensing signal using a single gas detecting sensor and controlling a ventilation system.

Another objective of the present invention is to provide a gas detecting device for detecting variation of an absolute value of the amount of a gas based upon a sensor signal received from a gas detecting sensor in a pulse width modulation (PWM) mode and performing digital signal processing, thereby realizing gas detection only with a low-priced signal processing device.

Additional features and advantages of the invention will be set forth in the following description, and in part will be apparent from the description, or may be learned by practice of the invention. The objectives and other advantages of the invention will be realized and attained by the structure as illustrated in the written description and claims hereof, as well as the appended drawings. To achieve these and other advantages, and in accordance with the purpose of the present invention as embodied and broadly described, a gas detecting sensor comprises: first and second sensing layers that respectively react to a gasoline exhaust gas and a diesel exhaust gas and are separately doped around an outer circumference of a sensor body; and first and second heaters for periodically heating the first and second sensing layers to different optimal reaction temperatures.

A gas detecting device of the present invention comprises: a gas detecting sensor; a sensor signal detecting unit for connecting internal resistance of a first sensing layer to internal resistance of a second sensing layer in the gas detecting sensor in parallel and connecting the internal resistance to an external fixed resistor in parallel to detect a sensor signal; a heater drive unit for periodically driving first and second heaters by turns; a PWM signal converting unit for detecting the sensor signal of the sensor signal detecting unit in a PWM mode at a predetermined time in synchronization with drive of the first or second heater; and a control unit implemented by a one chip microprocessor for controlling the first and second heaters periodically, controlling the PWM signal converting unit to receive the sensor signal, converting the sensor signal into a digital signal, and generating a control signal for controlling a ventilation system based upon a result of comparison of the digital signal and a predetermined reference value.

As illustrated, the present invention includes separately formed sensing layers for sensing gases and heaters for heating the sensor to different temperatures at which the respective sensing layers have optimal sensing characteristics. The two sensing layers are connected in parallel and a parallel resistance value is detected as a sensor signal. The sensor signal is converted into a PWM signal for gas detection. Accordingly, the present invention realizes a compact sensor and simplification of the gas detecting device. The present invention senses two different kinds of gases using a single sensor and discriminates the sensor signal by the kinds of gases through simple signal processing. The present invention detects the concentration of a sensed gas in aspect of an absolute value on the basis of a gas sensing data in the clean air and estimates a pollution level.

It is to be understood that both the foregoing general description and the following detailed description are exemplary and explanatory and are intended to provide further explanation of the invention as claimed.

BRIEF DESCRIPTION OF THE ATTACHED DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF PREFERRED EMBODIMENT

Reference will now be made in detail to the preferred embodiments of the present invention, examples of which are illustrated in the accompanying drawings.

With reference to the accompanying drawings, the embodiments of the present invention will now be described in detail.

Figure 1A:
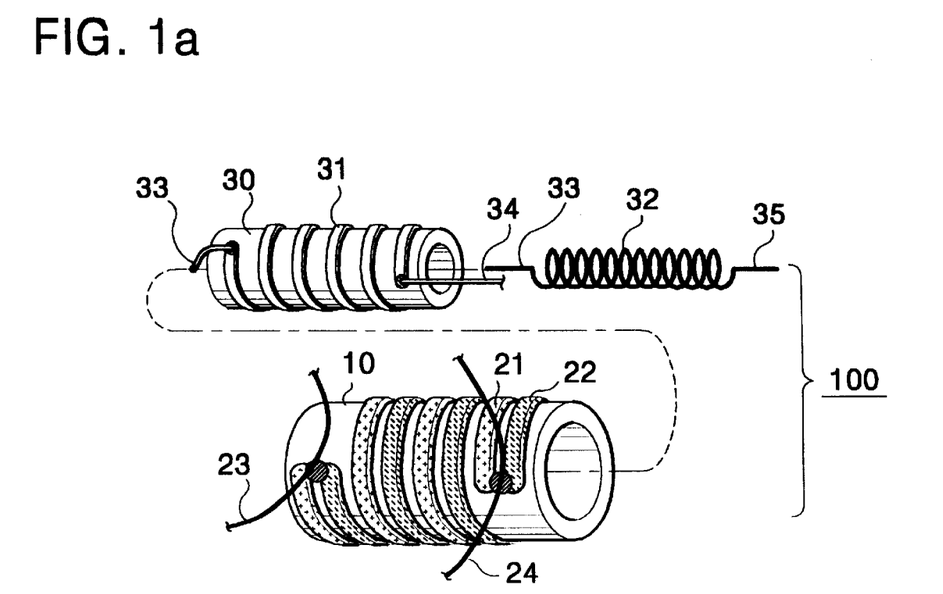
FIGS. 1a and 1b show a structure of a gas detecting sensor according to the present invention.
Figure 1B:
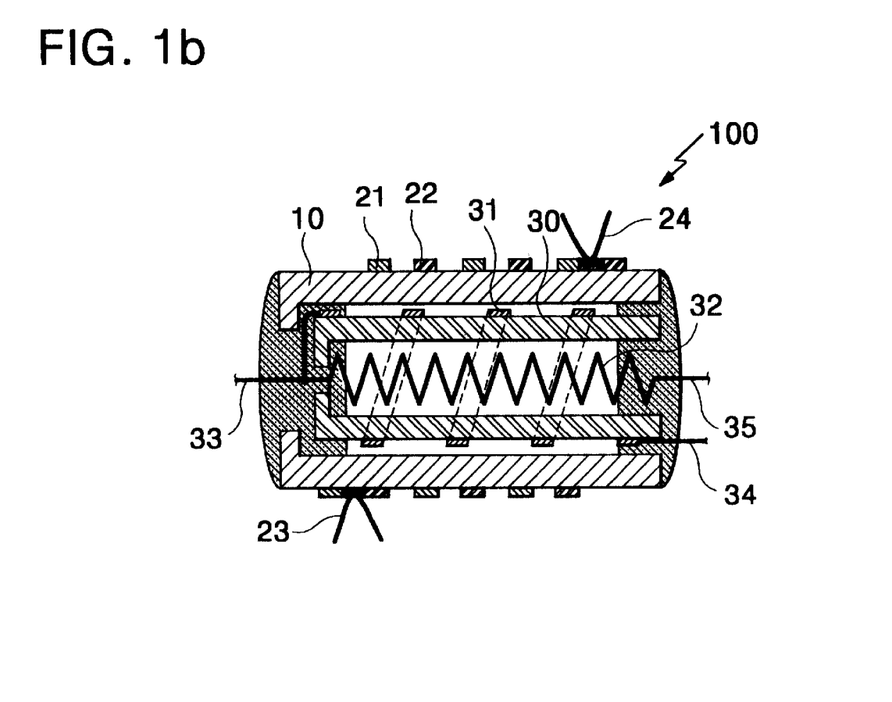

FIG. 1 shows a structure of a gas detecting sensor according to the present invention. As shown in FIG. 1, the gas detecting sensor comprises: a sensor body 10 which is formed of a ceramic cylinder and constitutes a trunk of the sensor; first and second sensing layers 21 and 22 that are separately doped around the outer circumference of the sensor body 10, have variable internal resistance values by respectively reacting to a gasoline exhaust gas and a diesel exhaust gas, and have both ends respectively connected to sensor wires 23 and 24 in common; and first and second heaters 31 and 32 that are inserted into the sensor body 10 and heat the first and second sensing layers 21 and 22 respectively reacting to the gasoline exhaust gas and the diesel exhaust gas to different optimal sensing temperatures. Both ends of the ceramic trunk are molded. For the first and second heaters 31 and 32, a conductive pattern constituting the first heater 31 is doped around the outer circumference of a heater body 30 of a ceramic cylinder that is inserted into the sensor body 10 and a coil constituting the second heater 32 is inserted into the heater body 30. The first and second heaters 31 and 32 are connected to each other at one end of the heater body 30 and commonly connected to a common ground wire 33. Reference numbers 34 and 35 indicate heater connection wires of the first and second heaters 31 and 32. In the gas detecting sensor as described above, the gasoline exhaust gas sensing layer 21 and the diesel exhaust gas sensing layer 22 are doped on the sensor body 10 forming separate spirals in parallel. The two heaters 31 and 32 are separately formed and connected to each other with a tap and the connected two-heater structure includes three terminals 33, 34, and 35.

Figure 2:
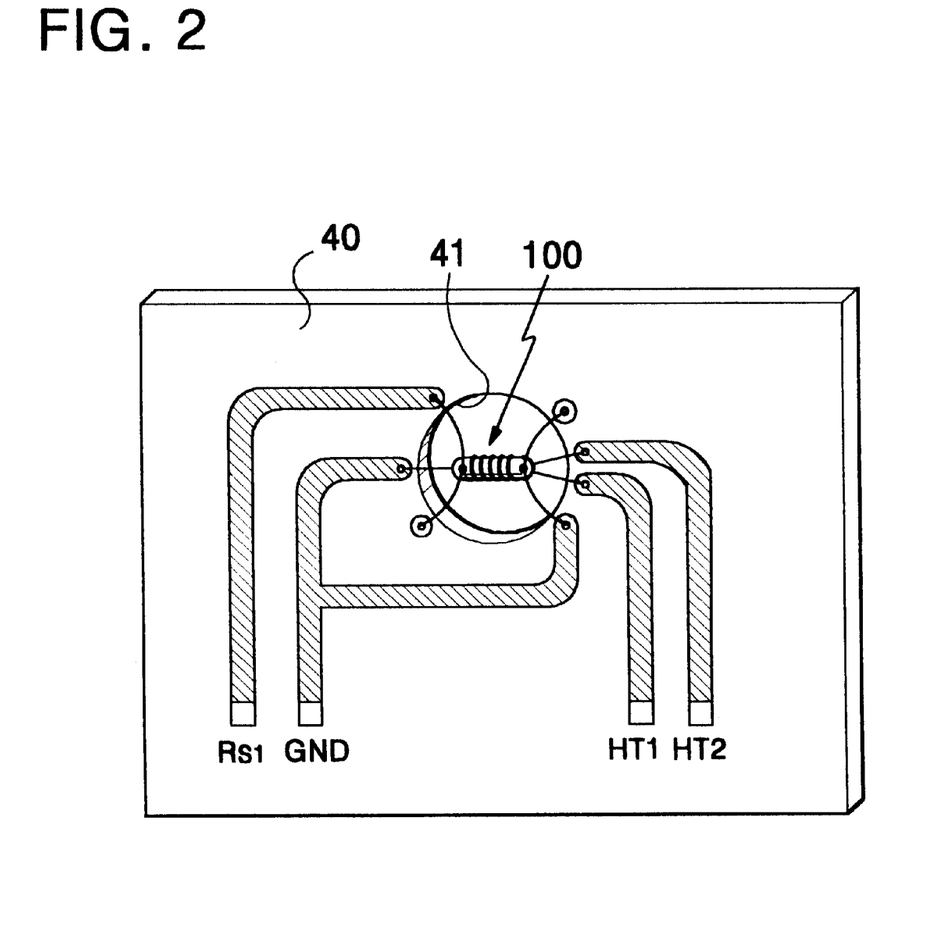
FIG. 2 is an exemplary diagram showing how a gas detecting sensor is installed according to the present invention.

FIG. 2 is a diagram showing an example of installation of the gas detecting sensor according to the present invention. As shown in FIG. 2, an aperture 41 is formed in a printed circuit board (PCB) 40 in which a signal line pattern is formed. The gas detecting sensor 100 is installed to be hung on the signal wires 23, 24, 33, 34, and 35 at the center of the aperture 41. Each wire is connected to each signal line in a conductive pattern.

Figure 3A:
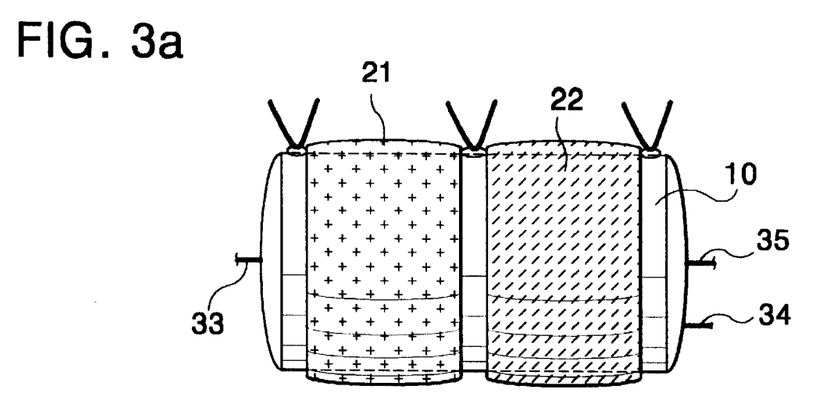
FIGS. 3a to 3c show different embodiments of a gas detecting sensor according to the present invention.
Figure 3B:
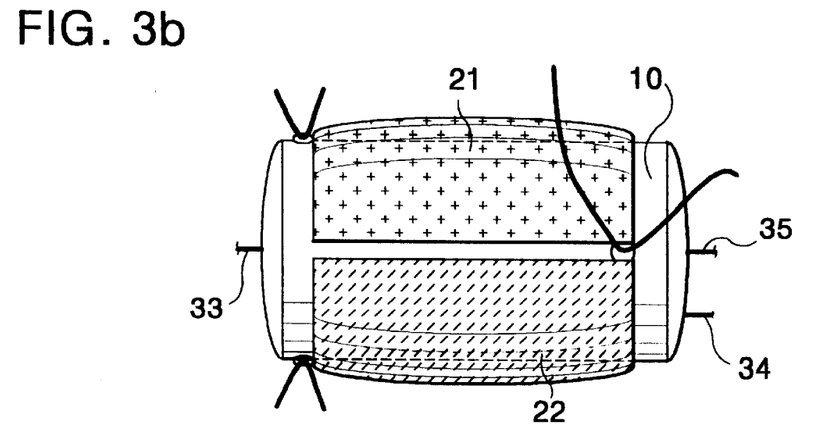
Figure 3C:
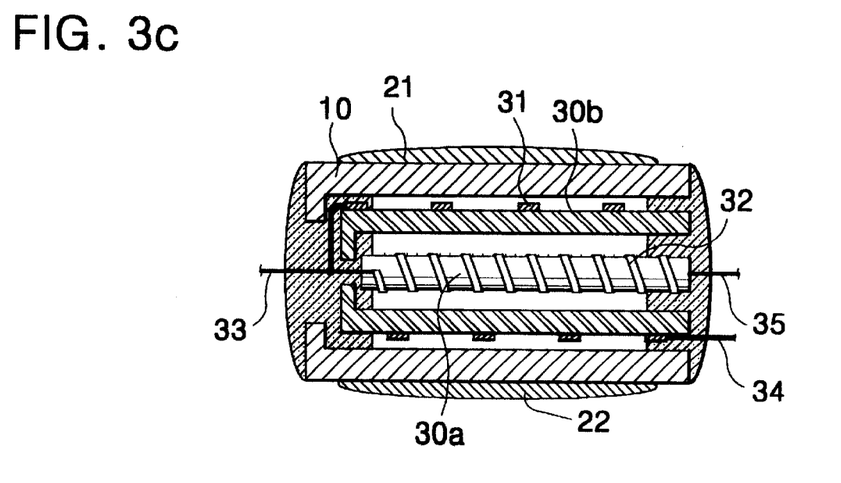

FIGS. 3a to 3c show different embodiments of the gas detecting sensor of the present invention. As shown in FIG. 3a, the first and second sensing layers 21 and 22 are separately doped at both left and right sides of the sensor body 10. A common wire connects the two sensing layers and sensor signal wires are respectively connected to the sensing layers 21 and 22 at both left and right ends of the sensor body 10. As shown in FIG. 3b, the first and second sensing layers 21 and 22 are separately formed on upper and lower parts of the sensor body 10. The sensing layers 21 and 22 are respectively connected to wires at both ends of the sensor body 10. As shown in FIG. 3c, the first and second heaters 31 and 32 are respectively formed on ceramic cylinders 30a and 30b having different diameters. One ceramic cylinder having one heater is inserted into the other ceramic cylinder having the other heater constituting an overall heater assembly. The heater assembly is inserted into the sensor body. A $SnO_2$ active layer that sensitively reacts to the gasoline exhaust gas but hardly reacts to the diesel exhaust gas is used for the first sensing layer 21. A $WO_3$ active layer that sensitively reacts to the diesel exhaust gas but hardly reacts to the gasoline exhaust gas is used for the second sensing layer 22.

Figure 8A:
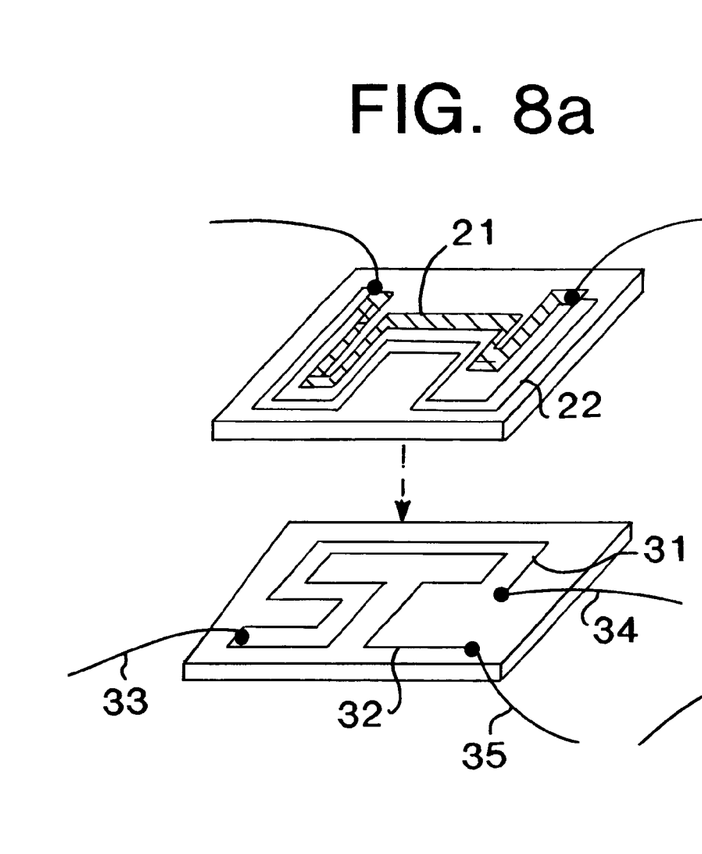
FIGS. 8a and 8b show different embodiments of the gas detecting sensor of the present invention.
Figure 8B:
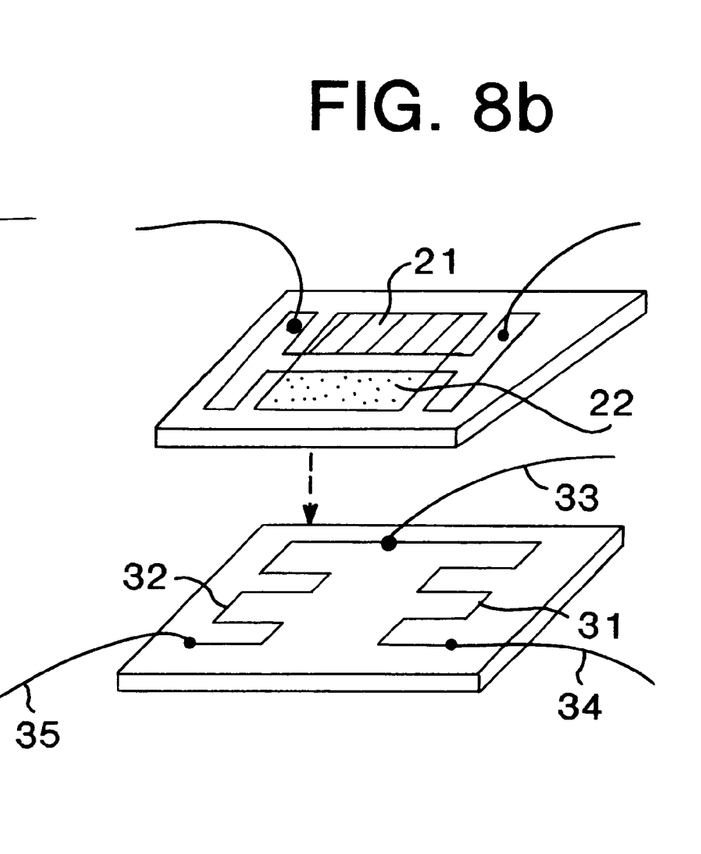

In the above embodiments, the sensor has a cylindrical shape, but it is not limited to that shape. FIGS. 8a and 8b show different embodiments of the gas detecting sensor of the present invention. A plate type sensor body where two kinds of sensing layers are separately doped and a plate type heater body including a first heater and a second heater are stacked and molded in a plate structure with the sensing layers being exposed. That is, the sensor body 10 is constructed with a plate ceramic substrate. $SnO_2$ and $WO_3$ is separately doped on the top of the plate ceramic substrate constituting the sensor body 10 in a predetermined pattern to form the first and second sensing layers 21 and 22. The first and second heaters 31 and 32 are constructed in such a manner that heater resistance is formed in a predetermined pattern on the top of a second plate ceramic substrate constituting the sensor body 10 and there is formed an intermediate tap for dividing a heater resistance value to supply temperatures proper to operate the respective first and second sensing layers 21 and 22, whereby the first and second heaters 31 and 32 are separately constructed. Finally, the resultant structure is so molded as to expose the sensing layers.

Figure 4:
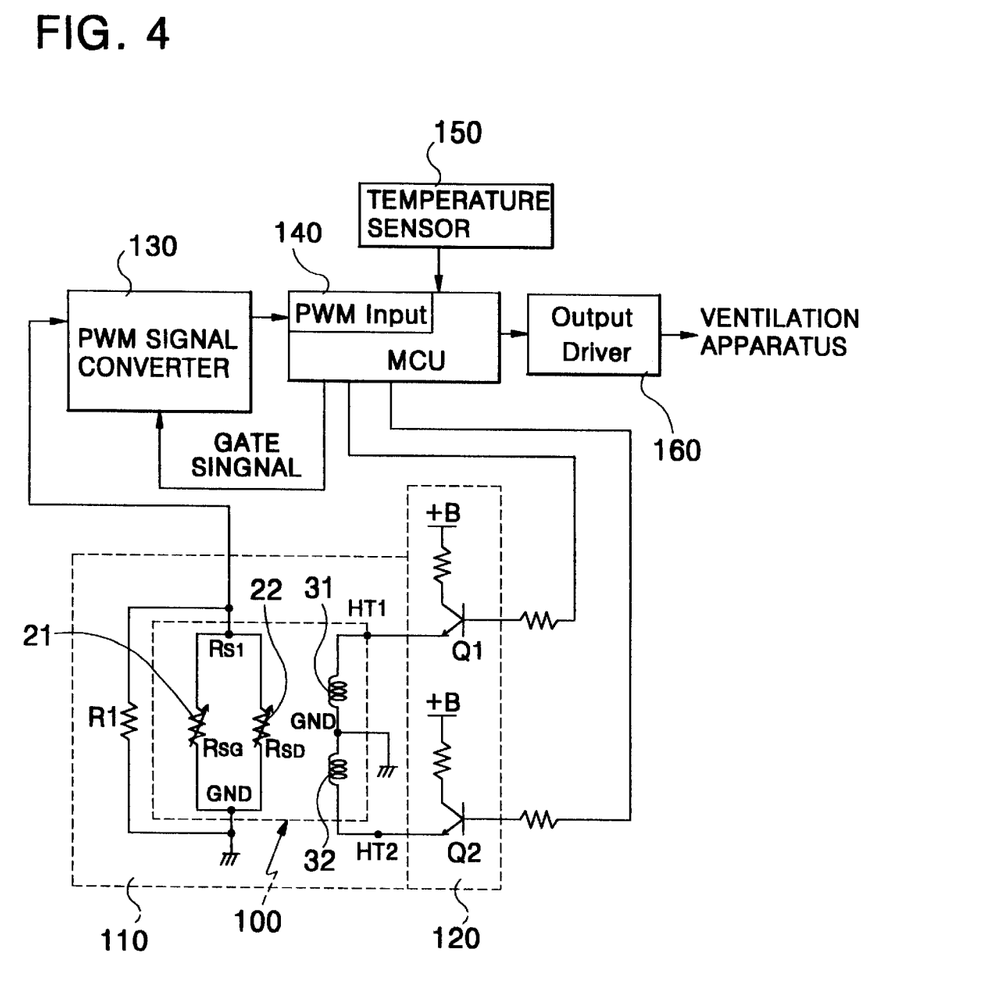
FIG. 4 is a diagram showing a configuration of a gas detecting device according to the present invention.

FIG. 4 shows a configuration of a gas detecting device of the present invention. As shown in FIG. 4, the gas detecting device comprises: the gas detecting sensor 100 including the first sensing layer 21 for sensing the gasoline exhaust gas and the second sensing layer 22 for sensing the diesel exhaust gas that are separately formed on a single sensor body and the first and second heaters 31 and 32 for heating the sensor to different temperatures for the purpose of sensing the gasoline and diesel exhaust gases; a sensor signal detecting unit 110 for connecting sensor resistance $R_{SG}$ and $R_{SD}$ of the first and second sensing layers 21 and 22 of the gas detecting sensor 100 in parallel, connecting the sensor resistance to a fixed resistor RI in parallel, and detecting variation of resistance values in response to the gasoline and diesel exhaust gases as a sensor signal; a heater drive unit 120 for periodically driving the first and second heaters 31 and 32 of the gas detecting sensor 100 by turns; a PWM signal converting unit 130 for converting the sensor signal from the sensor signal detecting unit 110 into a PWM signal at a predetermined time point in relation with the drive of the first and second heaters 31 and 32; and a control unit 140 constituted by a one chip microprocessor for periodically controlling the first and second heaters 31 and 32 by turns, controlling the PWM signal converting unit 130 to receive the sensor signal as the PWM signal, comparing the sensor signal with a prescribed reference value to decide a pollution level, and generating a control signal for controlling the ventilation system based upon the pollution level to the ventilation system via an output drive unit 160. The gas detecting device may further comprise a sensor temperature sensing unit 150 for sensing the temperature of the gas detecting sensor 100 and controlling operating times of the first and second heaters 31 and 32.

The sensor signal detecting unit 110 can realize a sensor which individually senses two kinds of exhaust gases with a single sensor assembly and a single sensor signal output line by forming the two sensing layers 21 and 22 in parallel. Through such structure, the sensor can be simplified and decreased in size, thereby simply constituting the gas detecting device. The intermediate tap 33 between the first and second heaters 31 and 32 is located at a division point having a heater resistance value allowing application of a temperature suitable for action of material sensing the gasoline and diesel exhaust gases. Namely, two heaters are obtained by placing the intermediate tap at a proper location in a single heater.

Figure 5:
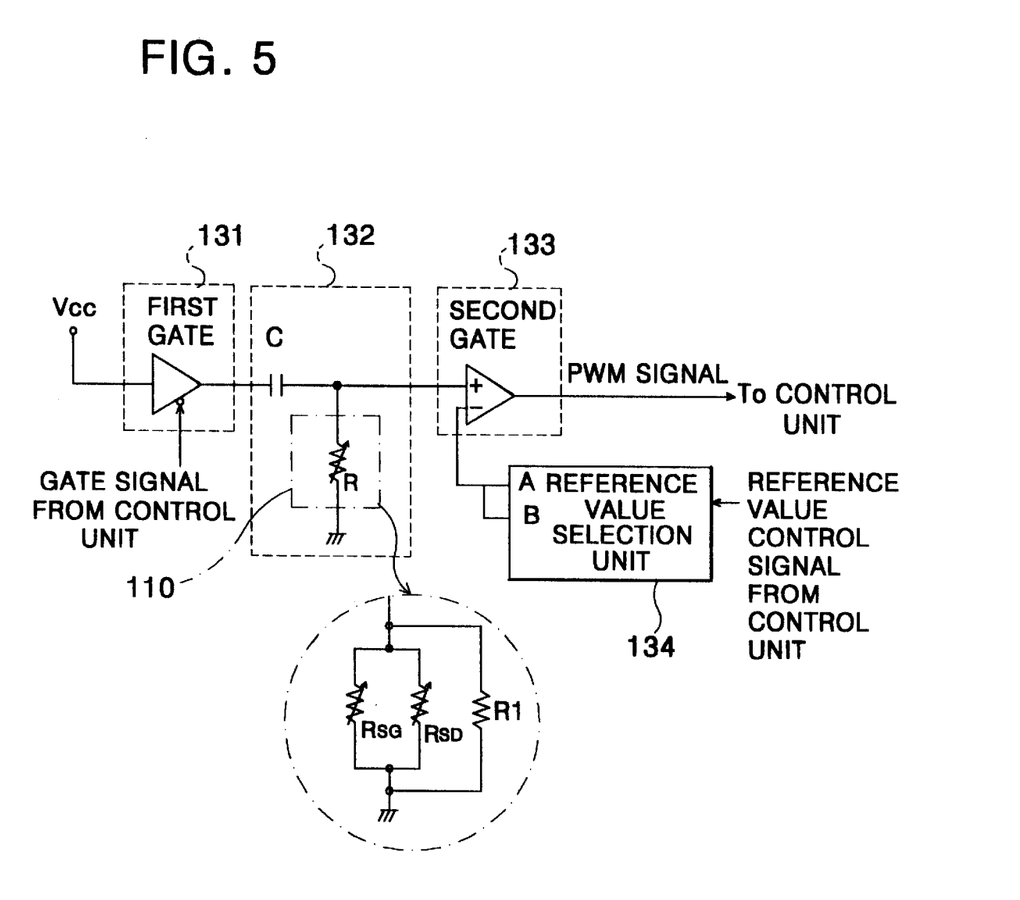
FIG. 5 is a diagram showing the PWM signal converting unit of a gas detecting device according to the present invention.

FIG. 5 shows a configuration of the PWM signal converting unit of the gas detecting device according to the present invention. As shown in FIG. 5, the PWM signal converting unit comprises: a first gate 131 for supplying DC voltage, Vcc, of a specified level according to control of the control unit 140; a differentiator 132 for differentiating an output of the first gate 131 with a condenser C and resistance R of and the sensor signal detecting unit 110; and a second gate 133 for converting an output waveform of the differentiator 132 into a PWM signal based upon the reference voltage. The reference voltage of the second gate 133 is one-half the output voltage, one-half ½ Vcc, of the first gate 131. The PWM signal converting unit may further comprise a reference value selection unit 134 for differently selecting a reference value for sensing the gasoline exhaust gas and a reference value for sensing the diesel exhaust gas according to control of the control unit 140.

The following concerns operation and effect of the present invention having such configuration as described above.

The gas detecting device of the present invention is based upon the characteristics that the reaction of the sensor changes depending upon the temperature of the gas sensing layer and each of the SnO₂ and WO₃ differentially reacts to the gasoline exhaust gas and the diesel exhaust gas. Typically a metallic oxide reacts to an oxidative gas better at a high temperature than at a low temperature. On the contrary, the typical metallic oxide reacts to a reductive gas better at the low temperature than the high temperature. The SnO₂ sensing layer is sensitive to the gasoline exhaust gas but rarely reacts to the diesel exhaust gas. The WO₃ sensing layer is sensitive to the diesel exhaust gas, but rarely reacts to the gasoline exhaust gas.

By applying these typical facts, the two kinds of exhaust gases can be sensed with only a single sensor and a pollution level can be determined through detection of a sensor signal and process of the signal. The sensor of the present invention uses SnO₂ for the first sensing layer 21 and WO₃ for the second sensing layer 22. The two sensing layers 21 and 22 are separately doped and connected to each other at both their ends in parallel in the circuit. For a heater, the first and second heaters 31 and 32 are provided to heat the sensing layers to different temperatures and periodically operated by turns to control the temperature of the sensor.

Figure 6A:
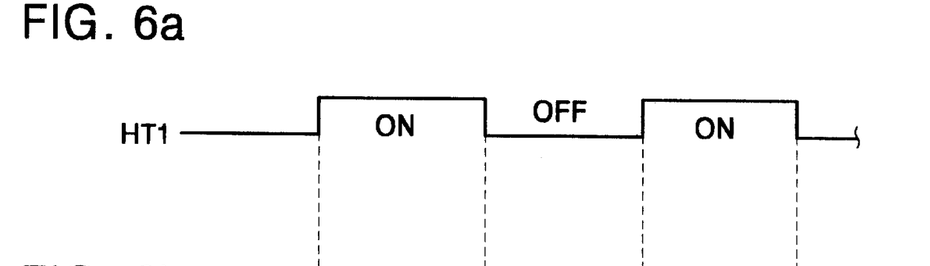
FIGS. 6a to 6d are illustrations for explaining drive of a heater, change of a temperature, and change of sensor resistance according to the present invention.
Figure 6B:
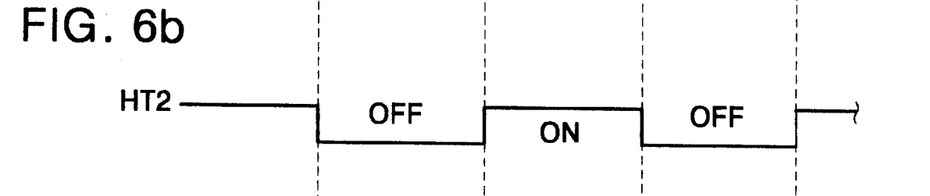
Figure 6C:
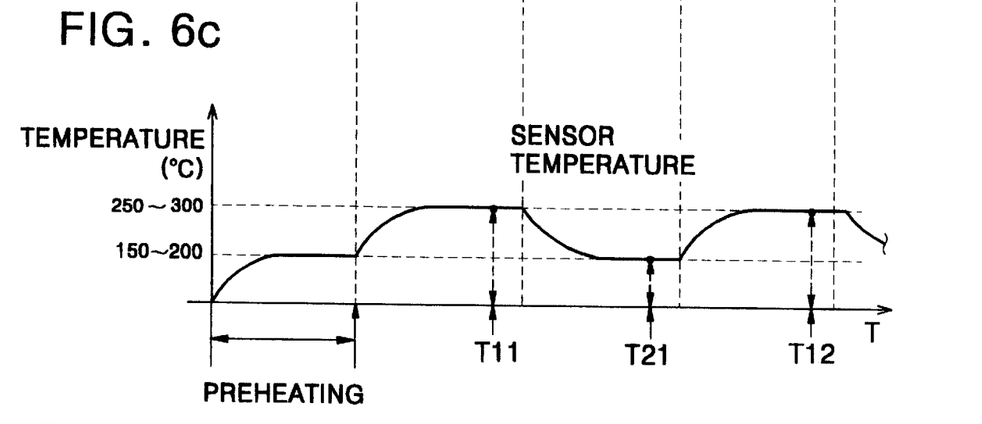

As shown in FIGS. 6a and 6b, the control unit 140 periodically turns ON and OFF the first heater 31 (HT1) and the second heater 32 (HT2) by turns. That is, the control unit 140 alternately controls the two heaters in a manner of dynamic heater driving. If alternately driving the two heaters HT1 and HT2, as shown in FIG. 6c, the sensor 100 is heated to different two temperatures. The SnO₂ sensor optimally reacts to the gasoline exhaust gas at 250~300 degrees centigrade. The WO₃ sensor optimally reacts to the diesel exhaust gas at 150~200 degrees centigrade. Accordingly, the first heater 31 heats the sensor 100 to 250~300 degrees centigrade and the second heater 32 heats the sensor to 150~200 degrees centigrade. When the sensor is differentially heated by the heaters 31 and 32, the first sensing layer 21 optimally reacts at 250~300 degrees centigrade and the second sensing layer 22 optimally reacts at 150~200 degrees centigrade.

Figure 6D:
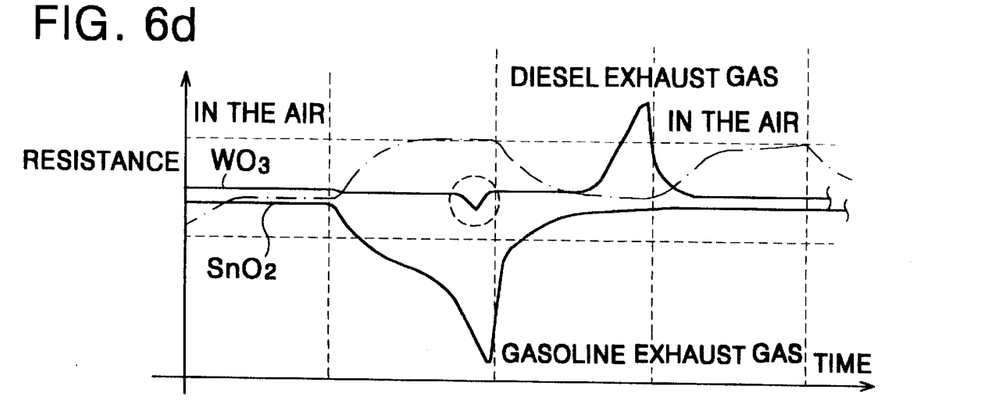

FIG. 6d shows variation of the resistance value of the gas detecting sensor 100. The first SnO₂ sensing layer 21 and the second and WO₃ sensing layer 22 maintain their respective basic resistance values in the clean air. If there is the gasoline exhaust gas in the air, the first sensing layer 21 reacts to the gas at 250~300 degrees centigrade and its resistance value decreases in proportion to the concentration of the gas. As the temperature decreases, the resistance value rapidly increases and returns to the basic resistance value. At this time, the second sensing layer of WO₃ reacts to the gasoline exhaust gas a little, so the resistance value of the second sensing layer decreases a little lower than the basic resistance value of the second sensing layer 22 when the gasoline exhaust gas is sensed at its highest concentration. However, the variation of the resistance value of the second sensing layer 22 reacting to the gasoline exhaust gas can be neglected through simple compensation. If there is diesel exhaust gas, the second sensing layer 22 reacts to the gas at 150~200 degrees centigrade and its resistance value increases as the concentration of the gas increases. As the temperature increases, the resistance value decreases towards the basic resistance value. At this time, the first sensing layer 21 hardly reacts to the diesel exhaust gas. In the gas detecting device of the present invention, the control unit 140 periodically controls the temperature of the sensor 100 to be 250~300 degrees centigrade and 150~200 degrees centigrade by turns and recognizes a sensor signal detected at the high temperature as a gasoline exhaust gas detection signal and a sensor signal detected at the low temperature as a diesel exhaust gas detection signal. As described above, the control unit 140 controls the temperature of the sensor and discriminates the gasoline exhaust gas detection signal from the diesel exhaust gas detection signal based upon the temperature at which the sensor signal is detected.

In another embodiment of the present invention, the sensor is heated to 250~300 degrees centigrade which is the temperature for sensing the gasoline exhaust gas when both first and second heaters 31 and 32 are all turned ON and the sensor is heated to 150~200 degrees centigrade which is the temperature for sensing the diesel exhaust gas when one of the two first and second heaters 31 and 32 is turned ON. The control unit 140 controls the first and second heaters 31 and 32 to adjust the temperature. The control unit 140 senses the gasoline exhaust gas after turning ON both heaters 31 and 32 and senses the diesel exhaust gas after turning ON a specified one of the two heaters 31 and 32.

In the sensor signal detecting unit 110 of the gas detecting device, the first sensing layer 21 is connected to the second sensing layer 22 in parallel and the two sensing layers 21 and 22 are connected to the fixed resistor R1 in parallel to detect a sensor signal. When the resistance of the first sensing layer 21 is represented with $R_{SG}$, the resistance of the second sensing layer 22 is represented with $R_{SD}$, and the fixed resistance is represented with R1, the detected resistance value R is expressed as:

$$R = \frac{\left(\frac{R_{SG} \times R_{SD}}{R_{SG} + R_{SD}}\right) \times R1}{\left(\frac{R_{SG} \times R_{SD}}{R_{SG} + R_{SD}}\right) + R1}.$$

Accordingly, each resistance value of the first and second sensing layers 21 and 22 hardly changes and is maintained at the corresponding basic resistance value at other temperatures than the corresponding reaction temperature, so the concentration of the gas sensed at the corresponding temperature can be detected. It happens that the $WO_3$ weakly reacts to the gasoline gas and its resistance value can be changed. However, the change is so little compared with the resistance value of the $SnO_2$ that it can be compensated based upon a compensation value obtained through tests during the signal processing and determination of variation of the resistance value by the control unit 140.

Figure 7A:
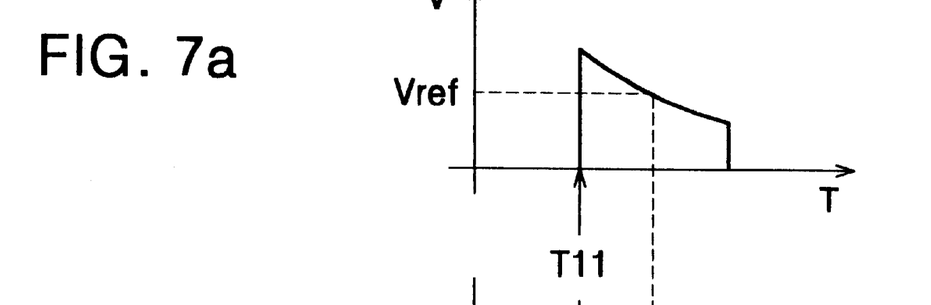
FIGS. 7a to 7d are graphs showing a relationship between resistance and PWM waveform and PWM signal conversion according to the present invention.
Figure 7B:
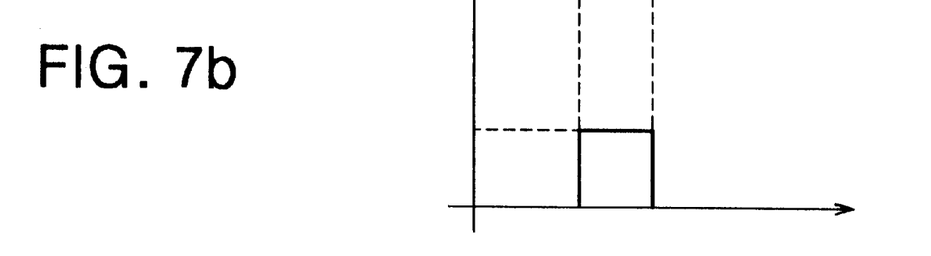
Figure 7C:
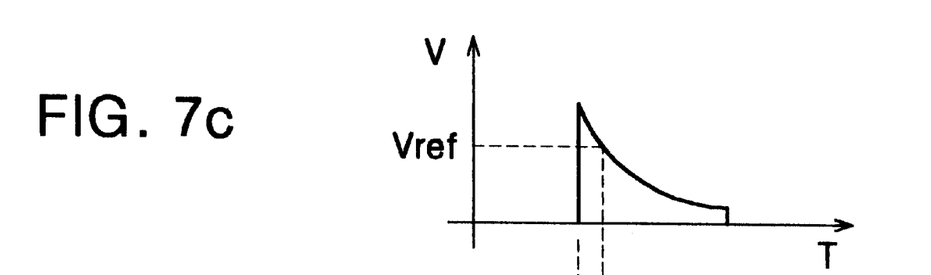
Figure 7D:
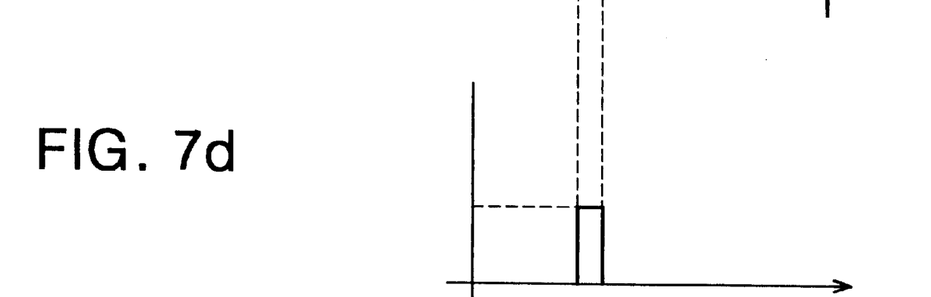

The PWM signal converting unit 130 makes the first gate 131 conduct electricity at the time when the gas detecting sensor is maintained at a proper temperature, after the first and second heaters 31 and 32 are driven by the control unit 140 and a specified period of time has passed as shown in FIG. 6c. That is, the first gate 131 is made to conduct electricity at points T11, T21, and T12 in FIG. 6c. The DC voltage, Vcc, is then applied through the first gate 131 and a differential waveform is generated by the condenser C of the differentiator 132 and the resistance R of the sensor signal detecting unit 110 whose parallel resistance value changes according to the sensing of a gas. The differential waveform, as shown in FIG. 7a, has an gentle slope when the condenser C and the resistance R responsive to the sensing of the gas have large values. On the other hand, when the condenser C and the resistance R responsive to the gas sensing have small values, the differential waveform has a steep slope as shown in FIG. 7c. The differential waveform changes in proportion to the value of the resistance R in the sensor signal detecting unit 110 responsive to the gas sensing. Only the differential waveform equal to or more than a reference value, Vref, is passed and the differential waveform less than the reference value, Vref, is intercepted at the second gate 133, so an output waveform of the second gate 133 appears as shown in FIG. 7b or FIG. 7d. That is, if the resistance value is larger, the output has a wider pulse as shown in FIG. 7b. If the resistance value is smaller, the output has a narrower pulse as shown in FIG. 7d. At this time, the pulse width is proportional to the magnitude of the resistance value changing according to the sensed concentration of the gas, so the width of the output pulse of the second gate 133 is related to the sensed gas concentration.

As described above, the PWM signal converting unit 130 makes the first gate 131 conduct electricity after the heater is driven by the control unit 140 for the specified period time (required for the temperature of the sensor to be maintained at a desired level in stable). The control unit 140 receives the PWM signal of the sensor signal from the second gate 133. The control unit 140 recognizes which heater was driven so that it can determine whether the input PWM signal is the gasoline exhaust gas sensing signal or the diesel exhaust gas sensing signal. Specifically, the control unit 140 recognizes the PWM signal generated after it drives the first heater 31 as the gasoline exhaust gas sensing signal while recognizing the PWM signal generated after it drives the second heater 32 as the diesel exhaust gas sensing signal.

The control unit 140 identifies digital data of the input PWM signal as gasoline exhaust gas sensing data or diesel exhaust gas sensing data and estimates a pollution level. The estimation of the pollution level is obtained by calculating a mean of the exhaust gas sensing data for a given unit time, comparing the mean value with reference data obtained in the clean air, and determining whether or not an absolute value of a difference between the mean value and the reference data goes beyond a predetermined limit. If pollution is determined, the control unit 140 controls the ventilation system to intercept the inflow of the air from the outside. The pollution level can be estimated in various ways. Pollution levels of the gasoline exhaust gas and the diesel exhaust gas may be separately estimated. The two kinds of exhaust gases may be generalized to is estimate an air pollution level. The estimation may also be performed variably according to surrounding circumstances. For such estimating ways, known methods applied in conventional ventilation control used in a vehicle or an air conditioner can be employed.

The $SnO_2$ sensing layer for sensing the gasoline exhaust gas decreases in its resistance value when it reacts to the gasoline exhaust gas. On the other hand, the $WO_3$ sensing layer for sensing the diesel exhaust gas increases in its resistance value when it reacts to the diesel exhaust gas. Accordingly, the magnitude of an absolute value of the gasoline exhaust gas sensing data is different from that of the diesel exhaust gas sensing data, so the control unit 140 estimates the concentration of each of the gasoline and diesel exhaust gases out of consideration for the magnitude of each absolute value. Since the sensing signals of the two kinds of gases have different magnitudes of their absolute values, the reference value of the second gate 133 may be differently applied for each gas to reduce a difference between the absolute value of the two gases during the estimation. For this purpose, there can be further provided with a reference value selection unit 134 for selecting one of a reference value for gasoline exhaust gas sensing and a reference value for diesel exhaust gas sensing as the reference value of the second gate 133. By differently selecting the reference value for the pulse width modulation, the difference between the absolute values of PWM signals of the two kinds of gases can be reduced. The estimation of a pollution level is attained by determining whether or not an absolute value of a difference between each data value and a reference value in the clean air goes beyond each predetermined limit that is established for each of the gasoline and diesel exhaust gases.

The sensor temperature sensing unit 150 is provided for sensing a temperature of the sensor 100 and controlling an operating time of the heater drive unit 120 based upon the sensed temperature. This helps the control unit 140 to automatically set the operating time of the heater out of consideration for external circumstances, such as local temperature characteristics, seasonal temperature characteristics, temperature characteristics according to places, and time based temperature characteristics when the device is used continuously.

As illustrated, the present invention provides a gas detecting sensor which effectively senses two kinds of gases having different reactions with only a single sensor. In addition, the present invention converts a sensor signal into a PWM signal, detects the signal without complex signal processing, and estimates a data value of the PWM signal to determine a pollution level. Compared with the conventional technique using two sensors, the present invention greatly simplifies the structure of a gas detecting device. Compared with the conventional technique using a single sensor, the present invention improves accuracy in estimation of a pollution level. The present invention is also realized without complex signal processing.

It will be apparent to those skilled in the art that various modifications and variations can be made in gas detecting sensor and device for controlling ventilation systems of the present invention without deviating from the spirit or scope of the invention. Thus, it is intended that the present invention covers the modifications and variations of this invention provided they come within the scope of the appended claims and their equivalents.

What is claimed is:

1. A gas detecting sensor comprising: a first sensing layer made of an active material sensitively reacting to a gasoline exhaust gas; a second sensing layer made of an active material sensitively reacting to a diesel exhaust gas; and first and second heaters for periodically heating said first and second sensing layers to respective optimal reaction temperatures, said first and second sensing layers being separately doped on a single sensor body and connected to each other in parallel, thereby sensing a gas based upon a variation of a parallel resistance responsive to gas sensing.

2. The gas detecting sensor as claimed in claim 1, wherein said sensor body is a ceramic cylinder, said first sensing layer is made of $SnO_2$, said second sensing layer is made of $WO_3$, said first and second sensing layers are separately doped on an external surface of said ceramic cylinder in a predetermined pattern, and said first and second heaters are configured such that a conductive pattern constituting the first heater is doped on an external surface of a heater body implemented by a ceramic cylinder inserted into said sensor body and a coil constituting the second heater is inserted into the heater body, said first and second heaters being commonly connected to a common ground wire at one end of said heater body.

3. The gas detecting sensor as claimed in claim 1, wherein said sensor body is a first plate ceramic substrate, said first sensing layer is made of $SnO_2$, said second sensing layer is made of $WO_3$, said first and second sensing layers are separately doped on a top surface of said first plate ceramic substrate in a predetermined pattern, and said first and second heaters are configured such that heater resistance is formed in a predetermined pattern on a top surface of a second plate ceramic substrate placed under said first plate ceramic substrate including said first and second sensing layers and an intermediate tap is disposed at a position where a heater resistance value is divided so as to supply appropriate temperatures for operation to said respective first and second sensing layers, thereby forming separate first and second heaters, said above elements being molded with said sensing layers exposed.

4. A gas detecting device for controlling a ventilation system, said device comprising:

a gas detecting sensor including a first sensing layer for sensing a gasoline exhaust gas and a second sensing layer for sensing a diesel exhaust gas that are separately formed on a single sensor body and first and second heaters for heating said sensor to different temperatures for the purpose of sensing the gasoline and diesel exhaust gases;

a sensor signal detecting unit for connecting sensor resistance of said first and second sensing layers of said gas detecting sensor in parallel, connecting the sensor resistance to a fixed resistor in parallel, and detecting variation of resistance values responsive to the gasoline and diesel exhaust gases as sensor signals;

a heater drive unit for periodically driving said first and second heaters of said gas detecting sensor by turns;

a pulse width modulation (PWM) signal converting unit for converting the sensor signal from said sensor signal detecting unit into a PWM signal at a predetermined time point after said first and second heaters are driven; and a control unit for periodically controlling said first and second heaters by turns, controlling said PWM signal converting unit to receive the sensor signal as the PWM signal, discriminating a gasoline exhaust gas sensing signal from a diesel exhaust gas sensing signal and estimating them, determining a pollution level based upon the estimation, and generating a control signal for controlling the ventilation system.

5. The gas detecting device as claimed in claim 4, further comprising a sensor temperature sensing unit for sensing a temperature of said gas detecting sensor and providing a sensed temperature to said control unit, thereby allowing said control unit to control operating times of said first and second heaters.

6. The gas detecting device as claimed in claim 4, wherein said PWM signal converting unit comprises:

a first gate made to conduct electricity for a predetermined time by control of said control unit, for providing DC voltage of a specified level;

a differentiator for differentiating an output of said first gate with a condenser and parallel resistance of said sensor signal detecting unit; and a second gate for converting an output waveform of said differentiator into said PWM signal based upon a reference voltage and providing an output.

7. The gas detecting device as claimed in claim 6, wherein said PWM signal converting unit further comprises a reference value selection unit for selecting one of two reference values that are differently set for respectively converting the gasoline exhaust gas sensing signal and the diesel exhaust gas sensing signal into PWM signals in advance under control of said control unit and for providing said selected reference value as a reference value for the pulse width modulation of said second gate.

* * * * *